United States Patent [19]
Salka et al.

[11] Patent Number: 5,494,659
[45] Date of Patent: Feb. 27, 1996

[54] HAIR TREATMENT COMPOSITION

[75] Inventors: Barry A. Salka, Fair Lawn, N.J.; Hermann Hensen, Haan, Germany; Holger Tesmann, Juechen, Germany; Joerg Kahre, Monheim, Germany

[73] Assignee: Henkel Kommanditgesellschaft auf Aktien, Duesseldorf, Germany

[21] Appl. No.: 109,790

[22] Filed: Aug. 20, 1993

[51] Int. Cl.⁶ .............................. A61K 7/075; A61K 7/08
[52] U.S. Cl. .................... 424/70.13; 424/70.28; 536/4.1; 536/6
[58] Field of Search ............... 424/70, 71; 536/4.1, 536/6

[56] References Cited

U.S. PATENT DOCUMENTS

| | | |
|---|---|---|
| 4,668,422 | 5/1987 | Malik et al. ............... 252/174.17 |
| 4,970,067 | 11/1990 | Panandiker et al. .......... 424/70 |
| 5,059,414 | 10/1991 | Dallal et al. ............... 424/70 |
| 5,120,531 | 6/1992 | Wells et al. ................ 424/70 |
| 5,120,532 | 6/1992 | Wells et al. ................ 424/70 |

FOREIGN PATENT DOCUMENTS

| | | |
|---|---|---|
| 0301298 | 7/1987 | European Pat. Off. |
| 0308189 | 3/1989 | European Pat. Off. |
| 0308190 | 3/1989 | European Pat. Off. |
| 0309259 | 3/1989 | European Pat. Off. |
| 0337354 | 10/1989 | European Pat. Off. |
| 3018600 | 11/1980 | Germany. |
| 03977 | 4/1990 | WIPO. |

OTHER PUBLICATIONS

Joacs, Preparation of Surfactants by Condensation of Fatty Acid Esters with Hydrolyzed Proteins, Muscio et al., vol. 59, 1982 pp. 217–221.
Fette und Oele Tenside Waschmittel, vol. 108, 1982, pp. 177–183—Abstract only.
SOFW–Journal, "Alkylpolyglucoside–Production and Application", vol. 118, 1992, pp. 894–903.
SOFW–Journal, "Development and Trends of Sugar Derived Surfactants", vol. 118, 1992, pp. 904–906.
Plantaren, Report from the 4th symposium of Cospha, 1992—Abstract only.

*Primary Examiner*—Shelley A. Dodson
*Attorney, Agent, or Firm*—Wayne C. Jaeschke; John E. Drach; Henry E. Millson, Jr.

[57] ABSTRACT

Hair treatment compositions containing (a) an alkyl polyglycoside of the formula I $$R^1O-[G]_p \qquad (I)$$

wherein $R^1$ is an alkyl or alkenyl radical having from 6 to 22 carbon atoms, G is a sugar unit having 5 or 6 carbon atoms and p is a number from 1 to 10; (b) a protein hydrolyzate having an average molecular weight in the range from 500 to 10,000 and, (c) a monomeric cationic surfactant provide hair with hold, body, stylability, strength and bounce.

20 Claims, No Drawings

HAIR TREATMENT COMPOSITION

BACKGROUND OF THE INVENTION

1. Field of the Invention

This invention relates to detergent mixtures containing alkyl or alkenyl oligoglycosides, also known as alkyl polyglycosides, protein hydrolyzates and monomeric cationic surfactants and the use of these mixtures for hair treatment.

2. Description of the Related Art

Washed hair can only be styled with difficulty and reluctance in view of the removal of grease and all soil particles. The creation and maintenance of a style which holds is complicated by the electrostatic charging which the hair undergoes. This is dependent upon the quality of the shampoo and the ambient air humidity level and is particularly noticeable in winter in warm and dry heating air. Accordingly, hair setting preparations are used to improve the combability of washed and towelled hair, for conditioning and for stabilization against external influences.

Commercial liquid hair setting preparations are solutions of film formers in water and/or alcohol. Plasticizers are also used to make the film on the hair more flexible. Cationic surfactants improve the combability of hair and reduce its electrostatic charging. The addition of perfume oils rounds off the end product, dyes being unnecessary, although they are often used on aesthetic grounds. Polymers, such as for example polyvinyl pyrrolidone and/or polyvinyl acetate, are typically used as the film formers. In view of the ever-increasing significance being attributed to the ecotoxicological properties of surfactants which come into contact with the human skin or hair, there is a continuing need for products which are ecologically acceptable not only as a whole, but also in regard to their individual ingredients.

Alkyl oligoglycosides, particularly alkyl polyglycosides, are nonionic surfactants which are acquiring increasing significance by virtue of their excellent detergent properties, their broad property spectrum and their high ecotoxicological compatibility. They have been used in combination with polymeric cationic materials for hair treatment.

The problem addressed by the present invention was to provide new hair setting preparations containing highly dermatologically safe and readily biodegradable film formers. Another problem addressed by the invention was to provide products which would be distinguished by improved removability by washing or brushing.

SUMMARY OF THE INVENTION

The present invention provides a composition useful for treating human hair to control the bounce or body thereof which comprises: (a) an alkyl polyglycoside of the formula I $$R^1O-(G)_p \qquad (I)$$

wherein $R^1$ is an alkyl or alkenyl radical having from 6 to 22 carbon atoms, G is a sugar unit having 5 or 6 carbon atoms and p is a number from 1 to 10; (b) a protein hydrolyzate having an average molecular weight in the range from 500 to 10,000 and, (c) a monomeric cationic surfactant. These compositions provide the hair with hold, body, stylability, strength and bounce in a way which has not hitherto been possible with conventional mixtures of polymers and cationic surfactants. The products can readily be washed out and brushed out and are distinguished by excellent dermatological and ecological compatibility. At the same time, the invention also includes in particular the observation that mixtures of alkyl and/or alkenyl oligoglycosides and protein hydrolyzates can act as film formers, a property which is otherwise known only of high-polymer systems.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about".

The alkyl or alkenyl polyglycosides which can be used in the compositions according to the invention may be derived from aldoses or ketoses containing 5 or 6 carbon atoms, preferably glucose. Accordingly, the preferred alkyl and/or alkenyl oligoglycosides are alkyl or alkenyl oligoglucosides. These materials are known generically as alkyl polyglycosides. The alkyl polyglycosides according to the invention have the formula (I)

$$R^1O-[G]_p \qquad (I)$$

wherein $R^1$ is an alkyl or alkenyl radical having from 6 to 22 carbon atoms, G is a sugar unit having 5 or 6 carbon atoms and p is a number from 1 to 10. The index p in general formula (I) indicates the degree of oligomerization (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is mostly a broken number. Alkyl or alkenyl oligoglycosides having an average degree of oligomerization p of 1.1 to 3.0 are preferably used. Alkyl or alkenyl oligoglycosides having a degree of oligomerization below 1.7 and, more particularly, between 1.2 and 1.4 are preferred from the applicational point of view.

The alkyl or alkenyl radical $R^1$ may be derived from primary alcohols containing 6 to 22 and preferably 8 to 16 carbon atoms. Typical examples are caproic alcohol, caprylic alcohol, capric alcohol, undecyl alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and technical mixtures thereof such as are formed, for example, in the hydrogenation of technical fatty acid methyl esters or in the hydrogenation of aldehydes from Roelen's oxo synthesis. Alkyl oligoglucosides based on hydrogenated $C_{8/6}$ coconut oil alcohol having a DP of 1 to 3 are preferred.

The protein hydrolyzates which can be used according to the invention are substances which are normally produced by degradation of animal protein, preferably bovine collagen. In alkaline hydrolysis, the peptide bonds are non-specifically opened in accordance with the rules of statistics. Since the carboxy groups of the peptides are present as salts during the hydrolysis while the amino groups are unprotected and can be partly eliminated, a hydrolyzate is obtained in which the polypeptides contain a larger number of carboxy groups than amino groups. Acidic hydrolysis also results in non-specific opening of the peptide bonds. In contrast to alkaline hydrolysis, however, the amino groups are present in salt form during the acidic degradation while the carboxy groups are present in free form but have a considerably higher stability than the unprotected amino groups.

Protein hydrolyzates which have been prepared by enzymatic methods are preferably used for the purposes of the invention. Enzymes acting specifically on the peptide bond are used in these methods. The products have a high homogeneity and, in particular, show improved dermatological compatibility in relation to the other hydrolyzates. The average molecular weight can be adjusted through the reaction conditions and, as with the alkaline and acidic hydrolyzates, is in the range from 500 to 10,000 and preferably in the from 2,000 to 6,000.

Protein hydrolyzates obtained by enzymatic degradation of vegetable protein are preferably used in addition to animal protein. Typical examples are hydrolyzates of soya protein, almond protein, wheat protein and/or potato protein. The protein hydrolyzates mentioned also have the advantage over animal products of improved dermatological compatibility.

The detergent mixtures may contain the alkyl or alkenyl oligoglycosides and the protein hydrolyzates in a ratio by weight of 1:5 to 5:1 and preferably in a ratio by weight of 1:3 to 3:1, based on the mixtures.

Suitable monomeric cationic surfactants are, for example, quaternary ammonium compounds of the formula (II)

wherein $R^2$ is an alkyl or alkenyl radical having from 6 to 22 carbon atoms, or a hydroxy-substituted alkyl or alkenyl radical having from 6 to 22 carbon atoms; $R^3$ is an alkyl or alkenyl radical having from 6 to 22 carbon atoms, a hydroxy-substituted alkyl or alkenyl radical having from 6 to 22 carbon atoms, or an alkyl radical containing 1 to 5 carbon atoms, each of $R^4$ and $R^5$ is an alkyl radical having from 1 to 5 carbon atoms; and X is halogen, phosphate, alkyl sulfate or alkyl phosphate.

The compounds of formula II are known substances which may be obtained by the relevant methods of preparative organic chemistry. One method for their production comprises, for example, quaternizing tertiary amines with methyl chloride or dimethyl sulfate.

Typical examples of compounds of the formula II suitable for use in accordance with the present invention are stearyl trimethyl ammonium chloride, distearyl dimethyl ammonium chloride, cetyl trimethyl ammonium chloride (Dehyquart® A, Henkel), dicetyl dimethyl ammonium chloride, 2-hydroxycetyl-2-hydroxyethyl dimethyl ammonium chloride (Dehyquart® E, Henkel) or hydroxyethyl ammonium phosphate (Dehyquart® SP, Henkel). Compounds in which $R^2$ is an optionally hydroxy-substituted alkyl radical containing 16 to 18 carbon atoms, $R^3$ has the same meaning as $R^2$ or represents a methyl or hydroxyethyl group, $R^4$ and $R^5$ represent methyl groups and X is chloride or methyl sulfate are preferably used.

Another group of monomeric cationic surfactants suitable for use in accordance with the invention are the esterquat of the formula (III)

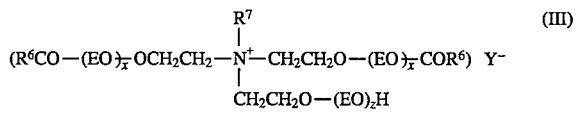

wherein $R^6CO$ is an aliphatic acyl radical having from 12 to 22 carbon atoms and 0 or 1 double bond, or a hydroxy-substituted aliphatic acyl radical having from 12 to 22 carbon atoms and 0 or 1 double bond; $R^7$ is a methyl group or a polyethylene glycol ether having 1 to 5 ethylene oxide units; each of x, y and z is a number from 0 to 5 such that the sum of x, y, and z is from 1 to 5; and Y represents halogen, alkyl sulfate or alkyl phosphate.

Esterquats are technical mixtures of optionally ethoxylated monofatty acid and difatty acid triethanolamine esters which are quaternized with ethylene oxide, alkyl halides, dialkyl sulfates or dialkyl phosphates. They are also known substances.

Esterquats which are derived from tallow fatty acid, coconut oil fatty acid and/or palm oil fatty acid having an iodine value of 0 to 40 and which have a degree of esterification of 1.5 to 1.9 are preferably used. The degree of ethoxylation may be 0 or 1 to 5 and is preferably 1 to 3. Esterquats corresponding to formula (I), in which $R^7$ is a methyl group or a polyethylene glycol chain containing 1 to 3 ethylene oxide units and Y is chloride or methyl sulfate, are particularly suitable from the applicational point of view. A methyl-quaternized dipalm oil fatty acid triethanolamine ester (Dehyquart® AU36, Pulcra/Barcelona) is particularly preferred.

The alkyl and/or alkenyl oligoglycosides and the monomeric cationic surfactants may be present in the detergent mixtures in a ratio by weight of 1:10 to 10:1 and preferably in a ratio by weight of 1:1 to 7:1, based on the mixtures.

The detergent mixtures according to the invention may be prepared simply by stirring, optionally at a slightly elevated temperature (30° to 40° C.). This is a purely mechanical process in which no chemical reaction takes place. Anhydrous or highly concentrated starting materials subsequently diluted with water to the desired in-use concentration may be used for the production of the detergent mixtures according to the invention. However, it is also possible to mix dilute solutions.

A particularly preferred composition is comprised of (a) an alkyl polyglycoside of the formula I

wherein $R^1$ is an alkyl or alkenyl radical having from 6 to 22 carbon atoms, G is a sugar unit having 5 or 6 carbon atoms and p is a number from 1 to 10; (b) a protein hydrolyzate having an average molecular weight in the range from 500 to 5,000 and, (c) a monomeric cationic surfactant.

The present invention also relates to a process for setting hair in which hair is treated in known manner with a detergent mixture comprising: (a) an alkyl polyglycoside of the formula I

wherein $R^1$ is an alkyl or alkenyl radical having from 6 to 22 carbon atoms, G is a sugar unit having 5 or 6 carbon atoms and p is a number from 1 to 10; (b) a protein hydrolyzate having an average molecular weight in the range from 500 to 10,000, preferably 500 to 5,000 and, (c) a monomeric cationic surfactant.

The detergent mixture is advantageously applied to and uniformly distributed on the washed and towel-dried hair in a quantity of, for example, 15 to 25 ml, depending on the body and length of the hair. It is useful to comb the hair through in order to ensure uniform distribution of the hair setting preparation. The hair is then rolled onto waterwave curlers and dried in air, preferably under a drying hood. However, instead of being rolled up, the hair may be styled and at the same time dried by means of a drying brush ("dryer setting").

The hair setting preparations are preferably used in the form of liquid aqueous and/or alcoholic, more particularly ethanolic, solutions having an active substance content of approx. 5 to 30% by weight and preferably 10 to 20% by weight, based on the solution. They may contain other additives such as, for example, film-forming polymers, such as polyvinyl pyrrolidone and/or polyvinyl acetate, dyes, perfumes, UV absorbers and thickeners. In addition to the liquid formulation, the preparations according to the invention may also be used in the form of foams ("setting foams").

The following Examples are intended to illustrate the invention without limiting it in any way.

EXAMPLE 1

Substances Used

A) Plantaren™ 2000, a product of Henkel KGaA, Düsseldorf, and is a $C_{8/16}$ alkyl oligoglucoside (DP=1.4)

B) Nutrilan® I, a product of CF Grünau, Illertissen/FRG Collagen hydrolyzate, average molecular weight approx. 4800

C) Ethyl alcohol, cosmetic, 96% by weight

D) Dehyquart® SP, a product of Henkel KGaA, Düsseldorf/FRG Hydroxyethyl ammonium phosphate II. Formulations

TABLE 1

Formulations used

| Formulation | Components (% by weight)* | | | |
|---|---|---|---|---|
| | A | B | C | D |
| A | 6.0 | 3.8 | 30.0 | 1.0 |
| B | 6.0 | — | 30.0 | 1.0 |

*ad 100 dist. water

EXAMPLE 2

Applicational Examples

To measure bounce, hair strands of the Alkinco "European Dark"—code 6634—type (length 12 cm, weight apoprox. 1 g) were treated with quantities of 250 mg water and setting preparation according to formulations A and B per strand. The setting preparations were applied to the damp hair. Formulation A corresponded to the invention while formulation B was used for comparison. In both cases, the setting preparations were adjusted to pH 6.6. After the treatment, the strands were applied without rinsing to curlers (diameter 48 mm) and dried for 2 h at 40° C. The vibration behavior of the curls in the uncombed and combed state was determined in 15% relative air humidity. The mean values of 10 measurements in regard to frequency, attenuation, O-amplitude, stretching force and stretching energy are set out in Tables 2 and 3.

TABLE 2

Examples according to the invention

| | | Attenuation | | O-Amplitude | | | |
|---|---|---|---|---|---|---|---|
| Ex. | F $s^{-1}$ | Min. $S^{-1}$ | Max. $S^{-1}$ | Min. mN | Max. mN | StF mN | StE mJ |
| 1a | 2.86 | 0.89 | 0.97 | 3.88 | 3.78 | 11.01 | 0.46 |
| 1b | 4.33 | 1.81 | 1.98 | 7.91 | 8.89 | 31.77 | 1.02 |
| 1c | 2.96 | 1.22 | 1.18 | 4.19 | 3.94 | 11.12 | 0.43 |
| 1d | 4.19 | 1.63 | 1.91 | 9.26 | 8.81 | 31.56 | 0.92 |

Legend:

TABLE 2-continued

Examples according to the invention

| | | Attenuation | | O-Amplitude | | | |
|---|---|---|---|---|---|---|---|
| Ex. | F $s^{-1}$ | Min. $S^{-1}$ | Max. $S^{-1}$ | Min. mN | Max. mN | StF mN | StE mJ |

F = Frequency
StF = Stretching force
StE = Stretching energy
Min. = Minimum
Max. = Maximum
a) Waterwave, curl not combed
b) Test formulation A, curl not combed
c) Waterwavel curl combed
d) Test formulation A, curl combed

TABLE 3

Comparison tests

| | | Attenuation | | O-Amplitude | | | |
|---|---|---|---|---|---|---|---|
| Ex. | F $s^{-1}$ | Min. $S^{-1}$ | Max. $S^{-1}$ | Min. mN | Max. mN | StF mN | StE mJ |
| C1a | 2.726 | 0.08 | 0.90 | 4.17 | 3.43 | 9.12 | 0.33 |
| C1b | 4.29 | 2.14 | 2.45 | 6.90 | 7.96 | 39.20 | 1.33 |
| C1c | 2.91 | 1.21 | 1.29 | 5.09 | 4.62 | 10.16 | 0.35 |
| C1d | 3.23 | 1.29 | 1.47 | 4.42 | 4.62 | 21.04 | 0.79 |

Legend:
a) Waterwave, curl not combed
b) Test formulation B, curl not combed
c) Waterwave, curl combed
d) Test formulation B, curl combed The Examples and Comparison Examples show that, compared with treatment with water alone (waterwave), formulations containing alkyl oligoglucosides and protein hydrolyzates as nonionic surfactants and formulations containing alkyl oligoglucosides alone as nonionic surfactants produce an improvement in bounce, as reflected in higher energies, vibration frequencies and initial amplitudes. In conjunction with the increased vibration, increased friction in the curls and hence increased attenuation are also observed. It makes no difference whether the curls are combed or uncombed.

In the case of uncombed curls, the effect is particularly clear because the strands which are stuck together have to be made to vibrate.

The vibration behavior of curls is illustrated in Table 4. The figures represent the attenuation of the maxima, the O-amplitude of the maxima and the stretching energy of the combed curls in 15% relative air humidity.

TABLE 4

Vibration behavior of curls

| Ex. | F | Attenuation $S^{-1}$ | O-amplitude mN | Stretching energy mJ |
|---|---|---|---|---|
| 2 | A | 1.90 | 8.90 | 0.93 |
| C2 | B | 1.45 | 4.75 | 0.79 |

Legend: F = Formulation

What is claimed is:

1. A hair treatment composition comprising: (a) an alkyl polyglycoside of the formula I $$R^1O\text{—}(G)_p \quad (I)$$

wherein $R^1$ is an alkyl or alkenyl radical having from 6 to 22 carbon atoms, G is a sugar unit having 5 or 6 carbon atoms and p is a number from 1 to 10; (b) a protein hydrolyzate having an average molecular weight in the range from 500 to 10,000 and, (c) a monomeric cationic surfactant.

2. The composition of claim 1 wherein $R^1$ is an alkyl radical having from 8 to 16 carbon atoms, G is a glucose unit and p is a number of 1 to 3.

3. The composition of claim 1 wherein said protein hydrolyzate has an average molecular weight in the range from about 2,000 to about 6,000.

4. The composition of claim 1 wherein said protein hydrolyzate is produced by degradation of an animal protein.

5. The composition of claim 1 wherein said monomeric cationic surfactant has the formula (II)

wherein $R^2$ is an alkyl or alkenyl radical having from 6 to 22 carbon atoms, or a hydroxy-substituted alkyl or alkenyl radical having from 6 to 22 carbon atoms; $R^3$ is an alkyl or alkenyl radical having from 6 to 22 carbon atoms, a hydroxy-substituted alkyl or alkenyl radical having from 6 to 22 carbon atoms, or an alkyl radical containing 1 to 5 carbon atoms, each of $R^4$ and $R^5$ is an alkyl radical having from 1 to 5 carbon atoms; and X is halogen, phosphate, alkyl sulfate or alkyl phosphate.

6. A hair treatment composition comprising:
(a) an alkyl polyglycoside of the formula I

wherein $R^1$ is an alkyl or alkenyl radical having from 6 to 22 carbon atoms, G is a sugar unit having 5 or 6 carbon atoms and p is a number from 1 to 10;
(b) a protein hydrolyzate having an average molecular weight in the range from 500 to 10,000; and
(c) a monomeric cationic surfactant of formula III:

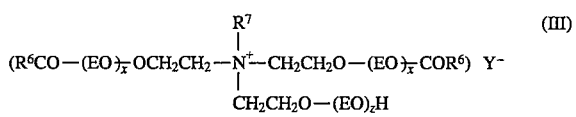

wherein $R^6CO$ is an aliphatic acyl radical having from 12 to 22 carbon atoms and 0 or 1 double bond, or a hydroxy-substituted aliphatic acyl radical having from 12 to 22 carbon atoms and 0 or 1 double bond; $R^7$ is a methyl group or a polyethylene glycol ether having 1 to 5 ethylene oxide units; each of x, y and z is a number from 0 to 5 such that the sum of x, y, and z is from 1 to 5; and Y represents halogen, alkyl sulfate or alkyl phosphate.

7. The composition of claim 1 wherein the weight ratio of components of (a)/(b) is from about 1:5 to about 5:1.

8. The composition of claim 1 wherein the weight ratio of components of (a)/(c) is from about 1:10 to about 10:1.

9. A process for setting hair which comprises applying a hair setting effective amount of a composition comprising:
(a) an alkyl polyglycoside of the formula I

wherein $R^1$ is an alkyl or alkenyl radical having from 6 to 22 carbon atoms, G is a sugar unit having 5 or 6 carbon atoms and p is a number from 1 to 10; (b) a protein hydrolyzate having an average molecular weight in the range from 500 to 10,000, and (c) a monomeric cationic surfactant.

10. The process of claim 9 wherein said protein hydrolyzate has an average molecular weight in the range from about 500 to about 1,000.

11. The process of claim 9 wherein $R^1$ is an alkyl radical having from 8 to 16 carbon atoms, G is a glucose unit and p is a number of 1 to 3.

12. The process of claim 9 wherein said protein hydrolyzate is produced by degradation of an animal protein.

13. The process of claim 9 wherein said monomeric cationic surfactant has the formula (II)

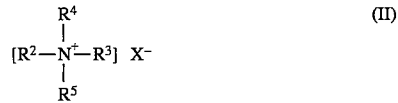

wherein $R^2$ is an alkyl or alkenyl radical having from 6 to 22 carbon atoms, or a hydroxy-substituted alkyl or alkenyl radical having from 6 to 22 carbon atoms; $R^3$ is an alkyl or alkenyl radical having from 6 to 22 carbon atoms, a hydroxy-substituted alkyl or alkenyl radical having from 6 to 22 carbon atoms, or an alkyl radical containing 1 to 5 carbon atoms, each of $R^4$ and $R^5$ is an alkyl radical having from 1 to 5 carbon atoms; and X is halogen, phosphate, alkyl sulfate or alkyl phosphate.

14. A process for setting hair which comprises applying a hair setting effective amount of a composition comprising:
(a) an alkyl polyglycoside of the formula I

wherein $R^1$ is an alkyl or alkenyl radical having from 6 to 22 carbon atoms, G is a sugar unit having 5 or 6 carbon atoms and p is a number from 1 to 10;
(b) a protein hydrolyzate having an average molecular weight in the range from 500 to 10,000; and,
(c) a monomeric cationic surfactant of formula III:

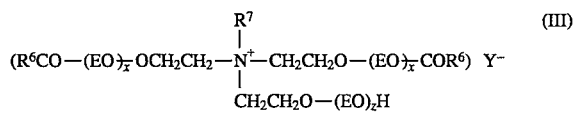

wherein $R^6CO$ is an aliphatic acyl radical having from 12 to 22 carbon atoms and 0 or 1 double bond, or a hydroxy-substituted aliphatic acyl radical having from 12 to 22 carbon atoms and 0 or 1 double bond; $R^7$ is a methyl group or a polyethylene glycol ether having 1 to 5 ethylene oxide units; each of x, y and z is a number from 0 to 5 such that the sum of x, y, and z is from 1 to 5; and Y represents halogen, alkyl sulfate or alkyl phosphate.

15. The process of claim 9 wherein the weight ratio of components of (a)/(b) is from about 1:5 to about 5:1.

16. The process of claim 9 wherein the weight ratio of components of (a)/(c) is from about 1:10 to about 10:1.

17. The composition of claim 4 wherein said protein hydrolyzate also contains a protein hydrolyzate produced by the enzymatic degradation of a vegetable protein.

18. The process of claim 12 wherein said protein hydrolyzate also contains a protein hydrolyzate produced by the enzymatic degradation of a vegetable protein.

19. The composition of claim 1 wherein the weight ratio of components (a):(b) is from about 1:3 to about 3:1, and the weight ratio of components (a):(c) is from about 1:1 to about 7:1.

20. The process of claim 9 wherein the weight ratio of components (a):(b) is from about 1:3 to about 3:1, and the weight ratio of components (a):(c) is from about 1:1 to about 7:1.

* * * * *

UNITED STATES PATENT AND TRADEMARK OFFICE
CERTIFICATE OF CORRECTION

PATENT NO. : 5,494,659
DATED : Feb. 27, 1996
INVENTOR(S) : Salka et al.

It is certified that error appears in the above-indentified patent and that said Letters Patent is hereby corrected as shown below:

In Col. 2, lines 21-23, please delete "$[G]_p$" and insert --$(G)_p$--.

In Col. 6, Table 3, line 25, please delete "2.726" and insert --2.72--.

Signed and Sealed this

Twenty-fourth Day of February, 1998

Attest:

BRUCE LEHMAN

*Attesting Officer*     *Commissioner of Patents and Trademarks*